(12) United States Patent  
Pacal et al.

(10) Patent No.: US 11,446,399 B2  
(45) Date of Patent: Sep. 20, 2022

(54) SYSTEM AND METHOD FOR QUANTIFYING THE PRESENCE OF CHEMICALS AND/OR PHYSICAL CONDITIONS IN OCULAR TISSUES

(71) Applicant: OPTIGGX INC., Toronto (CA)

(72) Inventors: Marek Pacal, Toronto (CA); Jeremy Michael Sivak, Toronto (CA); Stefan Wilhelm, Moore, OK (US); Desmond Fonn, Toronto (CA)

(73) Assignee: OPTIGGX INC., Toronto (CA)

( * ) Notice: Subject to any disclaimer, the term of this patent is extended or adjusted under 35 U.S.C. 154(b) by 301 days.

(21) Appl. No.: 15/733,121

(22) PCT Filed: Nov. 20, 2018

(86) PCT No.: PCT/CA2018/051477  
§ 371 (c)(1),  
(2) Date: May 20, 2020

(87) PCT Pub. No.: WO2019/095080  
PCT Pub. Date: May 23, 2019

(65) Prior Publication Data  
US 2020/0397920 A1 Dec. 24, 2020

Related U.S. Application Data

(60) Provisional application No. 62/588,533, filed on Nov. 20, 2017.

(51) Int. Cl.  
*G01J 3/30* (2006.01)  
*A61K 49/00* (2006.01)  
*A61B 3/14* (2006.01)

(52) U.S. Cl.  
CPC .......... *A61K 49/0013* (2013.01); *A61B 3/145* (2013.01)

(58) Field of Classification Search  
CPC ...... A61K 49/0013; A61B 3/145; A61B 3/10; C09K 2211/1007; C09K 2211/1011; C09K 2211/1033; C09K 2211/185; C09K 11/07; G02C 7/04  
USPC ........................................................ 356/316  
See application file for complete search history.

(56) References Cited

FOREIGN PATENT DOCUMENTS

| CA | 2438141 A1 | 6/2002 |
| CA | 2500877 A1 | 4/2004 |

*Primary Examiner* — Md M Rahman  
(74) *Attorney, Agent, or Firm* — DLA Piper, LLP US

(57) ABSTRACT

A system for quantifying the presence of at least one chemical and/or a physical condition in ocular tissues is provided. The system uses a membrane having at least one photo-reactive chemical- and/or physical condition-sensing indicator dye and a photo-reactive reference dye wherein both the photo-reactive chemical- and/or physical condition-sensing indicator dye and the photo-reactive reference dye are responsive to the same wavelength of an excitation light source but emit different wavelengths of light in a light spectrum. An optical data detector receives the emitted light and a processor splits the data into two or more colours of the light spectrum and measures the intensity of the two or more colours. The colour intensity belonging to the emitted light from the chemical- and/or physical condition-sensing indicator dye is compared to the colour intensity of the light emitted from the reference dye and the amount of chemical present and/or the extent of physical condition is ratiometrically determined therefrom.

16 Claims, 11 Drawing Sheets

|  | Viability (% surviving cells, compared to the no lens control) |
|---|---|
| No lens | 100% |
| Control contact lens | 91 ± 12 % |
| Oxygen-sensing contact lens | 86 ± 7 % |

SYSTEM AND METHOD FOR QUANTIFYING THE PRESENCE OF CHEMICALS AND/OR PHYSICAL CONDITIONS IN OCULAR TISSUES

TECHNICAL FIELD

The present disclosure relates to a system, method and use of chemical- and physical condition-sensing dyes for the qualification of chemical and physical conditions in ocular tissues.

BACKGROUND

The eye is an organ exceptionally sensitive to disturbances in oxygen delivery and distribution. Such disturbances are often associated with vision-compromising disorders such as corneal swelling and inflammatory processes on the ocular surface, cataract formation in the lens or degeneration of the retina and the optic nerve.

For example in diabetic retinopathy (DR), a disease that a large number of diabetics are at risk of developing, the metabolic effects of chronic hyperglycemia result in weakening and eventual leakage of retinal blood vessels. Accordingly, the abilities of the retinal vasculature to deliver oxygen and of the retina to consume oxygen are impaired. This eventually leads to retinal damage. Diabetes also impairs metabolism and oxygen consumption of the cornea and the lens, which can affect corneal health and may lead to lenticular cataracts. Furthermore, diabetes predisposes individuals to other retinal diseases including age-related macular degeneration (AMD) and glaucoma.

AMD is the leading cause of blindness in adults over the age of 60. The macula, a region in the retina responsible for high-resolution vision, needs a rich blood supply. Deficits in oxygen supply to the macula lead to hypoxia and oxidative stress (e.g., production of reactive oxygen species, ROS), which in turn causes neuronal death and vision loss, as a consequence. Glaucoma is an umbrella term for blinding diseases characterized by neuronal loss in the retina and deterioration of the optic nerve. Hypoxia and oxidative stress-caused neuronal damage are also implicated in the development of these diseases.

Over 20 million (~15%) adults in Canada and the United States are currently diagnosed with some form of ocular disorder. The clinical diagnosis of diseases such as AMD, glaucoma and DR relies on the loss of visual acuity and detectable changes in retinal anatomy and function. These symptoms may take years and even decades to develop to the point where they are noticed by an individual and lead one to seek medical help. By this stage, irreparable damage to the eye has already occurred. These disorders also suffer from a lack of reliable and fast responding biomarkers, which further challenges a diagnosis, and the assessment of any pharmaceutical or other medical intervention.

Apart from aging and diabetes, oxygen delivery, distribution and metabolism in ocular tissues can be upset by injury, medications, surgery, or other interventions.

For example, medication overdoses can cause adverse interactions but also chronic administration of the recommended drug doses may lead to ocular toxicity and vision loss. The mechanism of ocular toxicity is complex but include damage and leaking of the retinal blood vessels, retinal and corneal damage and cataracts.

It is also well established that contact lens wear compromises corneal oxygen consumption, creating hypoxic conditions. Corneal hypoxia induces metabolic changes in the corneal epithelium, which in turn may result in stromal swelling and inflammation leading to scarring and vision loss. Importantly, aging and diabetic patients are at higher risk of developing corneal damage due to contact lens wear.

Recognition of the early signs of eye toxicity and corneal hypoxia are essential in preventing vision impairment and loss. Unfortunately, as it is in the case of ocular diseases caused by aging and diabetes, the lack of reliable biomarkers makes an early diagnosis of these ailments difficult in the clinical practice.

Currently available methods for detecting oxygen levels and consumption in the eye require highly specialized clinical equipment and skills. This makes the use of ocular oxygen monitoring unsuitable as a routine diagnostic method.

For example, video fluorescein angiography (VFA), requiring the intravenous injection of fluorescent dye-fluorescein, or spectrophotometric techniques (retinal oximetry), assessing ocular blood vessel oxygen saturation have been used to infer the supply of oxygen in the eye. However, these methods are either invasive or generally non-quantitative. Furthermore, these methods have limited spatial resolution and their sensitivity is limited by corneal opacities, cataracts, and blood vessels occlusions and hemorrhages; all common ocular issues in later stages of retinopathy.

Some of the shortcomings of the above-noted techniques have attempted to be addressed through the use of magnetic resonance imaging (MRI). MRI can be used both invasively to quantify the absolute oxygen levels and non-invasively to quantify the spatial changes in eye oxygenation. However, as a drawback to the use of MRI in assessing ocular oxygen levels compared to, for example, the above-noted optical techniques, MRI offers almost a hundred-fold lower spatial resolution. Additionally, MRI requires the use of large and expensive equipment, which further limits the use of this method on large-scale routine bases in many populations.

Oxygen levels and consumption within ocular tissues can also be measured directly through the use of specialized polarographic (Clark) electrodes. However, this method is not only technically demanding but also invasive when intra-ocular oxygen levels are measured. Even when used non-invasively, for example when applied to the corneal surface, electrodes can only provide spatially- and temporally-limited information. Another problematic drawback to the use of electrodes is that some oxygen is consumed during the actual measurement. When measuring low oxygen concentrations, this can be particularly problematic. Despite the shortcomings and difficulties associated with the Clark oxygen electrodes, this method has provided important insights into oxygen consumption and distribution defects in diabetic patients. For example, compared to non-diabetic controls, adults with Type 1 diabetes display approximately a 20% reduction in corneal oxygen uptake and similar reduction in oxygen levels in the conjunctiva (membrane covering the front of the eye beyond cornea and lining the inside of the eyelid). Compared to non-diabetics, adults with Type 2 diabetes, display approximately a 10% reduction in the corneal oxygen uptake and conjuctival oxygen levels.

It would accordingly be advantageous to provide a simple, non-invasive method allowing accurate oxygen quantification in ocular tissues.

SUMMARY

It is desirable to develop a clinically relevant simple system and method capable of providing an accurate quantification and high-resolution spatial distribution of oxygen as well as other chemicals in the eye. Furthermore, a better understanding of the roles oxygen plays in ocular diseases may facilitate the design of improved ocular disorder treatments and reliable drug efficacy assessments as well as the ability to detect and diagnose oxygen-related disorders in the eye earlier than allowed by current techniques. Better oxygen quantification techniques may also help in the monitoring of corneal damage caused, for example, by cytotoxicity and contact lens wear.

Diabetic patients display reduced oxygen uptake into the cornea and exhibit lower oxygen levels in the conjunctiva. Accordingly, it would be desirable to develop a system that could assist in the monitoring of oxygen levels in the anterior ocular tissue in diabetics and could be utilized as an ophthalmic diagnostic method. Moreover, given the prevalence of oxygenation defects in vision-compromising disorders, such a method may be widely clinically applicable in several different disorders aside from diabetes, as noted above.

In one aspect a system is described for quantifying the presence of at least one chemical and/or physical condition in the anterior ocular tissue. The system comprises a membrane including at least one photo-reactive chemical- and/or physical condition-sensing indicator dye and a photo-reactive reference dye where both of the at least one photo-reactive chemical- and/or physical condition-sensing indicator dye and the photo-reactive reference dye are responsive to substantially the same wavelength of light from an excitation light source and capable of luminescing in different regions of a light spectrum. An optical data detector capable of detecting light emitted from the at least one photo-reactive chemical- and/or physical condition-sensing indicator dye and the photo-reactive reference dye in response to light from said excitation light source is also provided. Information from the optical data detector is fed to a processor capable of splitting the detected luminescence into two or more colour components of the light spectrum and measuring the intensity of the two or more colour components. The processor is further capable of ratiometrically determining the concentration of at least one chemical and/or the extent of at least one physical condition as a function of luminescence from at least one chemical- and/or physical condition-sensing indicator dye compared to the reference dye.

In some embodiments the membrane further includes a second photo-reactive chemical- and/or physical condition-sensing indicator dye.

In some preferred embodiments the optical data detector is a digital camera that captures a digital image, which may be incorporated into a smartphone. In some embodiments, the optical detector is a spectrometer which provides spectral analysis.

In some preferred embodiments, the processor includes software capable of measuring a pixel intensity of two or more colour components so as to ratiometrically determine said concentration of said at least one chemical and/or the extent of at least one physical condition as a function of luminescence from said at least one chemical- and/or physical condition-sensing indicator dye compared to said reference dye. In some embodiments, the processor includes software capable of measuring spectral intensities of two or more colour components so as to ratiometrically determine said concentration of said at least one chemical and/or said extent of at least one physical condition as a function of luminescence from said at least one chemical- and/or physical condition-sensing indicator dye compared to said reference dye. Furthermore in some embodiments the detected light is in the visible spectrum or near infrared spectrum and the processor splits said detected light into red, green and blue components. Thus, in some embodiments, the luminescence beyond the visible range for example, in the near infrared spectral region, may also be detected in some embodiments.

In some embodiments the at least one photo-reactive chemical-sensing dye is responsive to oxygen and is a porphyrin-based dye. In preferred embodiments, the at least one photo-reactive chemical-sensing indicator dye is a metalloporphyrin dye. In some embodiments the reference dye is non-responsive to oxygen and excitable at the same/similar wavelength as the chemical-sensing indicator dye. In preferred embodiments, the reference dye is a polycyclic aromatic hydrocarbon-based dye.

In some embodiments, the membrane further includes an outer layer of variable permeability. In preferred embodiments, the outer layer is a contact lens.

In some embodiments, the membrane will remain in a liquid or partially liquid form and will be used as such on the anterior ocular tissue.

In some embodiments, the at least one chemical is a gas which may be, for example, oxygen or, carbon dioxide. In some other embodiments the at least one chemical is an ion which may be $Na^+$, $K^+$ or $H^+$ (pH).

In some embodiments, the at least one physical condition is temperature.

In another aspect, there is provided a method for quantifying the presence of at least one chemical and/or physical condition in the anterior ocular tissue. The method comprises providing a membrane including at least one photo-reactive chemical- and/or physical condition-sensing indicator dye and a photo-reactive reference dye to the anterior ocular tissue, both of the at least one photo-reactive chemical- and/or physical condition-sensing indicator dye and the photo-reactive reference dye responsive to substantially the same wavelength of light from an excitation light source and capable of luminescing in different regions of a light spectrum;

providing light from the excitation light source so as to cause the at least one photo-reactive chemical- and/or physical condition-sensing indicator dye and the photo-reactive reference dye to luminesce;

providing an optical data detector capable of detecting light emitted from the at least one photo-reactive chemical- and/or physical condition-sensing indicator dye and the photo-reactive reference dye in response to the light;

providing data from the optical data detector to a processor capable of splitting the detected light into two or more colour components of the light spectrum and measuring the intensity of the two or more colour components; and ratiometrically determining the concentration of the at least one chemical and/or the extent of at least one physical condition as a function of luminescence from the at least one chemical- and/or physical condition-sensing indicator dye compared to the reference dye In some embodiments of the method, the membrane further includes a second photo-reactive chemical- and/or physical condition-sensing indicator dye.

In some embodiments of the method, the optical data detector is a digital camera, which may be incorporated into a smartphone, that captures a digital image. In some embodiments, the optical detector is a spectrometer which provides spectral analysis.

In some embodiments of the method, the processor includes software capable of measuring a pixel intensity of the two or more colour components so as to ratiometrically determine the concentration of the at least one chemical and/or the extent of the at least one physical condition as a function of luminescence from the at least one chemical- and/or physical condition-sensing indicator dye compared to the reference dye. Furthermore, in some embodiments of the method, the processor includes software capable of measuring spectral intensities of the two or more colour components so as to ratiometrically determine the concentration of the at least one chemical and/or the extent of the at least one physical condition as a function of luminescence from the at least one chemical- and/or physical condition-sensing indicator dye compared to the reference dye.

In some embodiments of the method, the detected light is in the visible spectrum and the processor splits the detected light into red, green and blue components. The luminescence beyond the visible range, for example in the near infrared spectral region, can also be detected in some embodiments.

In some embodiments of the method, the at least one photo-reactive chemical-sensing dye is responsive to oxygen and is a porphyrin-based dye, preferably a metalloporphyrin dye. In some embodiments of the method the reference dye is a polycyclic aromatic hydrocarbon-based dye, and preferably coumarin-based or diphenylanthracene-based dye.

In some embodiments of the method, the membrane further includes an outer layer of variable permeability. Furthermore, in some embodiments of the method, the outer layer is provided as a contact lens.

In some embodiments of the method, the membrane will remain in a liquid or partially liquid form and will be used as such on the anterior ocular tissue.

In some embodiments of the method, the at least one chemical is a gas and may be oxygen or carbon dioxide. Furthermore, in some embodiments, the at least one chemical is an ion and may be $Na^+$, $K^+$, or $H^+$ (pH).

In some embodiments of the method, the at least one physical condition is temperature.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

Exemplary embodiments are described by way of example only, with references to the accompanying drawings, wherein:

FIG. 7b is a regression plot of the luminescence intensity ratio of the spectrum plots of FIG. 7a;

DETAILED DESCRIPTION

Figure 1:
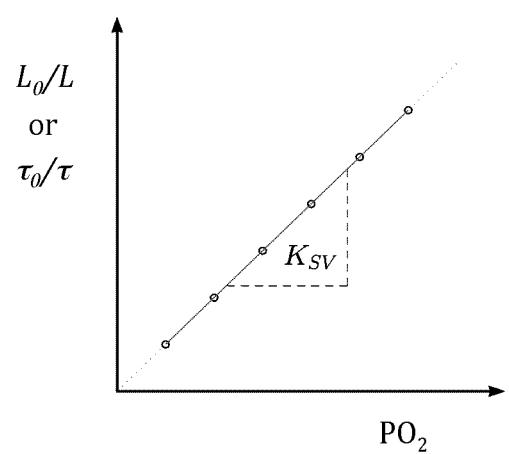
FIG. 1 is a regression plot of the Stern-Volmer equation.

Optical sensing technology is a technique that uses indicator dyes that change optical properties in the presence of a chemical analyte or in response to a varying physical condition. When such a dye absorbs light, its electrons enter an excited state followed by the emission of light with a longer wavelength, a phenomenon known as luminescence.

Briefly, the luminescence intensity and lifetime of such dyes are affected by the presence of the given chemical or physical condition and can thus be used to quantify these parameters. A whole range of sensors has been developed that respond to analytes such as gases (e.g., $O_2$, $CO_2$) or ions (e.g., $Na^+$, $K^-$) and changes in pH and temperature and are contemplated in various embodiments of the instant disclosure. These optical analyte-sensing dye sensors may offer a sensitive and non-invasive means of chemical quantification which are well suited for in vivo applications.

Unlike the oxygen-sensing and qualification techniques noted above the use of luminescent dyes may provide for high-resolution measurements of oxygen concentration over an extended area and thus provide spatial patterns of oxygen distribution. Furthermore, such dyes do not consume oxygen as part of the luminescent process and thus may provide more accurate levels of oxygen present and provide the detection of oxygen at very low levels. Such features may allow for a non-invasive, simple and accurate quantification of oxygen on the anterior ocular surface.

The exposed anterior (front) part of the eye is the most obvious place where measurement of oxygen quantification in ocular tissues could be taken. Indeed, much could be learned about the ocular health from the anterior surface of the eye. For example, the reduction of oxygen uptake into the cornea and of the oxygen levels in the conjunctiva (membrane covering the front of the eye beyond cornea and lining the inside of the eyelid) correlates with the progression of retinopathy in diabetic patients.

It is also important to note that while oxygen is the main focus of this disclosure, the ocular ailments discussed above lead to a large array of chemical and physical changes in the ocular tissues, including the anterior eye surface. For example, aging and diabetes lead to increases in tear fluid osmolarity, i.e. increases in the concentrations of ions such as sodium ($Na^+$) and potassium ($K^+$). It is also suggested that the temperature of the anterior eye surface decreases as a consequence of decreased metabolic rates in the aging and diabetic ocular tissues. Further, corneal hypoxia due to contact lens wear leads to changes in $CO_2$ levels and acidosis (lowering of pH). Unfortunately, as in the case of oxygen, it is not trivial to detect and monitor these chemical and physical changes in vivo, let alone in clinical practice, which limits the use of the former as clinical biomarkers.

The use of indicator and reference dyes is briefly explained below in relation to the instant disclosure.

With reference to FIG. 1, it is shown that the luminescence intensity and lifetime of an oxygen-sensing dye employed in the instantly disclosed system are dynamically quenched (diminished) by oxygen. The extent of quenching, in the simplest case, is proportional to the oxygen concentration, following the Stern-Volmer equation of $$L_0/L=1+K_{sv}[O_2], \text{ or } \Box_0/\Box=1+K_{sv}[O_2]$$

where:
$L_0/L$=luminescence intensity in the absence/presence of $O_2$;
or
$\Box_0/\Box$=luminescence lifetime in the absence/presence of $O_2$
$K_{sv}$=Stern-Volmer constant (dye-dependent); and
$[O_2]$=oxygen concentration.

Therefore, the Stern-Volmer equation can be used to quantify the amount of oxygen present. In the ideal case, this relationship is linear. Accordingly, changes in an indicator dye's actual luminescence intensity (or lifetime) may be used to quantify oxygen levels in various settings, such as a clinical application. For example, oxygen-sensing dyes (or other chemical-sensing indicator dyes) may be embedded into specialized fiber-optic probes or polymer films and micro/nano particles, for in vitro and in vivo applications. The indicator dye's luminescence intensity quenching can be directly measured by a spectrometer. Alternatively, by using indicator dyes whose emission spectra are detectable by an RGB digital camera chip, the luminescence intensity can be read from the pixel intensities of the red (R), green (G) or blue (B) channels of the acquired image or other suitable data form. Luminescence lifetime-based probes may also be used, requiring more complex electronics. The recent development of CMOS (complementary metal-oxide semiconductor) image sensors for lifetime imaging may lead to the development of simpler lifetime measuring systems.

Figure 2:
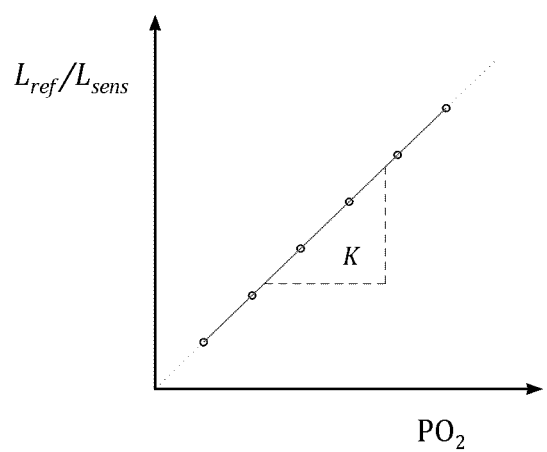
FIG. 2 is a regression plot of the linear equation of the ratiometric oxygen quantification.

Luminescence intensity, unlike luminescence lifetime, may be affected by a variety of factors, for example by dye concentration, photo-bleaching, or light source intensity. Thus intensity-based oxygen sensing is preferably ratiometric. For this purpose, a reference—oxygen independent—dye is used in various embodiments of the disclosed system. In the instantly disclosed system, a reference dye is chosen such that it is excitable at the same wavelength as the above-noted oxygen-sensing dye, yet both dyes are chosen to have distinct emission spectrums. Therefore, oxygen concentration, or other dye-measurable parameter(s), may be determined from the ratio of the luminescence intensities of the indicator and the reference dyes measured at two different emission wavelengths. In some embodiments, a sensing dye (e.g., oxygen-sensing dye) possessing two distinct emission peaks, an oxygen-dependent one and the other oxygen-independent can be used. In such scenario, a distinct reference dye is not needed, as such dual-emitting dye is self-referencing. As in the Stern-Volmer relationship, the ratiometric sensing method follows a linear dependency between luminescence intensity and oxygen concentration (FIG. 2):

$$L_{ref}/L_{sens}=K[O_2],$$

where:
$L_{ref}/L_{sens}$=reference/oxygen-sensing dye luminescence intensity;
K=quenching constant; and
$[O_2]$=oxygen concentration.

The oxygen-sensing dyes suitable for use in some embodiments of the instant disclosure are members of the metalloporphyrin class. These dyes contain a flat ring of four linked heterocyclic groups with a central metal ion such as platinum(II) ($Pt^2$). They can be easily synthesized and are non-toxic. Metalloporphyrins are embedded into a solid polymer layer or used in a solution and can detect oxygen in its gaseous form or dissolved in liquids at a large temperature range (−80° C.-+80° C.). They are unaffected by changes in pH, salinity and ionic strength, making them suitable for use in the instant application. Metalloporphyrin dyes have a long shelf-life (years) and display exceptional photo-stability. For example, metalloporphyrin dyes can be exposed to light for hours with minimal photo-bleaching. Without wishing to be bound by theory, when embedded in oxygen-permeable materials, metalloporphyrins may respond to changes in oxygen concentration within seconds, thus the necessary exposure time to detect oxygen levels may be very brief. Once calibrated, such oxygen-sensing dyes may be repeatedly used without losing its sensitivity.

With reference to the eye, the ocular surface is normally covered with a thin (<10 μm) film of tears. Tears are made up of water (pH 7.4) containing ions such as sodium, potassium or chloride, traces of proteins (enzymes, antibodies, mucins) and lipids. Since metalloporphyrins display robust behavior in a range of conditions, these mild conditions are unlikely to have a noticeable effect. Metalloporphyrin oxygen-sensing dyes thus make an ideal candidate for use in the instant application. However, it is contemplated that other dyes capable of sensing and providing an indicator for changes in oxygen level, and detection of other elements, molecules and chemicals may be suitable. With the use of metalloporphyrin oxygen-sensing dyes the inventors have not observed any effect of the tear fluid on optical properties of the oxygen-sensing dye.

The instantly disclosed system and method pertains to a contact lens having an oxygen-sensing layer whose luminescence intensity changes can be detected by a spectrometer or a digital imaging device, such as many smart-phone cameras. The luminescence intensity can be converted into a numerical value, which is compared to a reference standard and quantification of corneal oxygen can be determined using a data processor.

The detection limit of metalloporphyrins for oxygen dissolved in liquid (such as the tear film covering the cornea) is 15 ppm (parts per million). However, other oxygen-sensing dyes have been developed with limits of oxygen detection as low as 5 ppb (parts per billion). For comparison, the oxygen concentration in the tear film is approximately 200,000 p.p.m (parts per million) by volume. As discussed above, Type 1 and 2 diabetics display approximately 20 and 10% reduction in corneal oxygen uptake from the tear film, respectively. Since the ability of diabetic cornea to take up oxygen from the tear film decreases with the severity of the disease, it is reasonable to speculate that earlier stages of diabetes and pre-diabetes affect the oxygen uptake to a lesser degree, when compared to non-diabetic controls. As shown and discussed in EXAMPLE 4 below, the diabetic corneal oxygen uptake defects were simulated by selectively restricting the access of rabbit corneal tissue to oxygen. We altered the tear film oxygen levels by means of utilizing contact lens materials of variable oxygen permeability. With this embodiment, changes were detected in tear oxygen levels as low as 0.8%. Therefore, the instant disclosure may be used to detect 10-20% difference in corneal oxygen uptake seen in diabetic patients and such method may be used to monitor the progression of their disease. Moreover, such method may also be used for detecting corneal oxygen defects in individuals as a diagnostic method for diabetes in earlier stages of the disease, including pre-diabetes, where the corneal oxygen uptake is expected to be reduced to a lesser degree. With the use of the instantly disclosed method, for example, pre-diabetic conditions and other ocular disorders may therefore be detected in individuals far before physical symptoms appear. In some embodiments of the instant disclosure, even more sensitive oxygen sensing dye may be used allowing for monitoring of oxygen changes in ultra-low ranges, allowing detection of even minuscule corneal oxygen defects and pushing the detection limits of, for example, diabetes and pre-diabetes even further.

Figure 3:
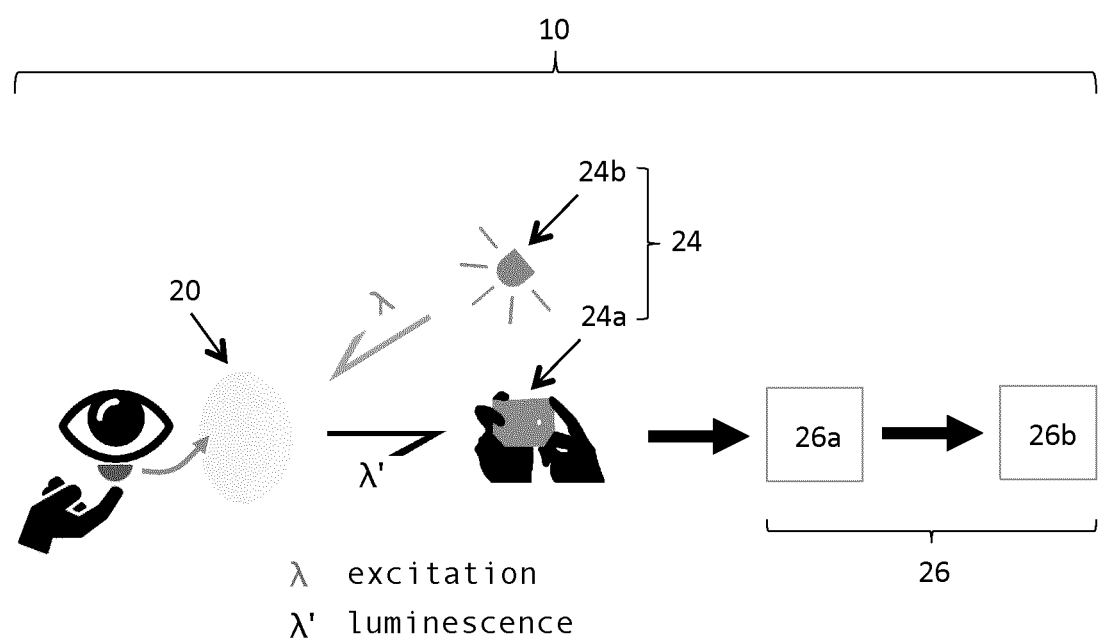
FIG. 3 is a schematic diagram of a system for detecting ocular oxygen levels in an exemplary embodiment of the instant disclosure.

Turning now to FIG. 3, there is generally shown the system 10 of the instant disclosure for non-invasively detecting ocular oxygen levels. Such a system, it is contemplated, may be useful in detecting other chemical analytes and physical conditions in the anterior ocular tissue using appropriate chemically reactive chemical sensing indicator dyes and reference dyes. Apart from oxygen, deregulation of many other chemical analytes and physical conditions have been associated with the progression of ocular diseases. It is contemplated that the instantly disclosed system may be modified to monitor these chemical analytes and physical conditions and thus validate them as potential ocular disease biomarkers. For example, diabetic patients with various stages of retinopathy consistently display increased levels of salt ions (e.g., sodium, potassium or calcium) in the tears. Conversely, patients with diabetic retinopathy (DR) and age related macula degeneration (AMD) show reduced ocular surface temperature; a consequence of compromised ocular blood flow. A variety of dyes with excitation and emission peaks in the visible or near infrared range of the electromagnetic spectrum can be utilized for ratiometric optical sensing of ions (e.g., ionophore-based ion-selective sensors) and temperature (e.g., rare earth-aluminum borate-based dyes). These analytes and physical conditions can be monitored separately or in various combinations. Indeed, probes detecting multiple analytes and physical conditions (including $O_2$, $CO_2$, pH and Temperature) have been developed and used in several in vitro and in vivo biological contexts and such may similarly be used in the instantly disclosed system.

Briefly, in addition to a chemical sensing membrane 30, in this exemplary system of the instant disclosure attached to a contact lens 20, being comprised of an oxygen-sensing indicator dye, for example a metalloporphyrin oxygen-sensing dye 28a and/or a reference dye 28b (see FIG. 4), the system may include two additional components: a hardware component 24 and a software component 26. The hardware component 24 is comprised of an optical data detector 24a and an excitation light source 24b. In some embodiments, as discussed in more detail below, the luminescence detection may be based on digital imaging or spectrophotometry. The software component 26 is provided to acquire image or data results from the optical detector 24a, manipulate and convert the optical data into a numerical (diagnostic) value via processor 26a which is then outputted as a numerical indicator of the, in this exemplary embodiment, oxygen levels 26b.

Figure 4:
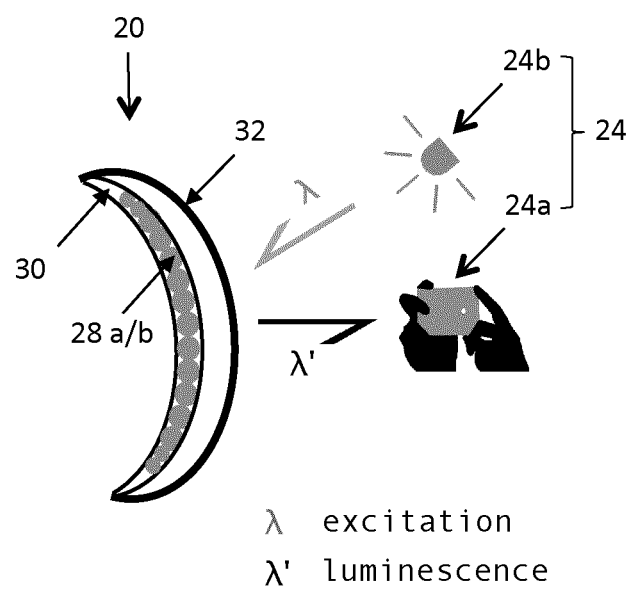
FIG. 4 is a schematic diagram of an excitation light source of FIG. 3 exciting an oxygen-sensing dye and a reference dye in a dye-containing contact lens of the instant system and an optical data detector capturing data of the light emitted from the dye-containing contact lens.

Generally, the oxygen-sensing contact lens having an oxygen-sensing indicator dye 28a applied to an eye-contacting membrane 30 as shown for example in FIG. 4, is installed over the ocular surface of an individual as a contact lens would normally be installed. The excitation light source 24b directs light at an outer surface 32 of the contact lens 20 and the optical detector 24a is used to capture an image or emitted light data. In FIGS. 3 and 4, $\lambda$ is used to denote an excitation light source 24b directing a desired wavelength of light at the contact lens 20 so as to cause the oxygen-sensing indicator dye 28a and the reference dye 28b to emit respective intensities of light which is captured by the optical data detector 24a and $\lambda'$ is used to denote the luminescence intensity of the oxygen-sensing indicator dye 28a and reference dye 28b captured by the optical data detector 24a.

The oxygen-sensing contact lens 20, shown in FIG. 4 may be comprised of two zones, an external zone or outer surface 32, and eye-contacting surface or zone 30, having oxygen-sensing or other chemical- and/or physical condition-sensing indicator 28a and reference dyes 28b therein accessible to oxygen from the individual's ocular surface. For example, the external zone or outer surface 32 may be made from materials of variable oxygen permeability so as to allow specific amounts of ambient oxygen pass through and may include light-filtering properties that will protect the sensing layer from excessive ambient light and may modify/filter the excitation light and the emission luminescence. The oxygen-sensing zone may be comprised of the oxygen-sensing or other chemical-sensing indicator 28a and reference dyes 28b embedded into a supportive oxygen-permeable or desired chemical-permeable matrix. The dyes may further be incorporated into micro/nano particles with various levels of permeability to oxygen or to another chemical analyte or physical condition. In some embodiments, the eye-contacting surface or zone 30 may also have light-filtering capability to prevent the excitation and emission light from entering the retina.

The oxygen-sensing or other chemical- and/or physical condition-sensing indicator dye 28a and the reference dye 28b are chosen such that both emit light when excited by the excitation light source 24b at the same wavelength $\lambda$. The intensity of the light emitted remains substantially constant with respect to the reference dye 28b, yet varies with respect to the oxygen-sensing dye or other chemical- and/or physical condition-sensing indicator 28a depending on the amount of oxygen or other chemicals present, for example on the ocular surface of an individual. $\lambda'$ emitted as detected by the optical data detector 24a can then be digitized and split into the various colours in the colour spectrum, for example Red, Green and Blue. The relative intensities of the Red, Green and Blue emitted light can then be quantified using software installed on the processor 26a. By comparing the intensity of emitted light in the colour spectrum from the oxygen-sensing or other chemical- and/or physical condition-sensing indicator dye 28a to the intensity of light in the colour spectrum from the reference dye 28b, the amount of oxygen on the ocular surface can be ratiometrically determined.

Therefore, the oxygen-sensing layer may be made up of a sensing "cocktail" comprised of, in some exemplary embodiments, an oxygen-sensing or other chemical- and/or physical condition-sensing indicator dye 28a, for example a porphyrin-based dye and a reference dye 28b which is oxygen-insensitive (or otherwise insensitive to chemicals and/or physical conditions to which it is desired to measure the level thereof) dye, embedded in a supporting polymer. In some exemplary embodiments, the sensing "cocktail" may be directly embedded in a silicone hydrogel-containing contact lens 20. In other exemplary embodiments, the supporting layer may be comprised of a biocompatible hydrogel applied to the inside of a contact lens 20 via suitable application methods. In some exemplary embodiments, such method may be pad printing.

The oxygen-sensing or other chemical- and/or physical condition-sensing indicator dye 28a and the reference dye 28b are chosen such that they are both excited to luminesce at substantially the same wavelength of light. Accordingly the emission intensity, but not the wavelength of the oxygen-sensing dye is therefore affected by the amount of the oxygen present. Whereas, in contrast, the emission of the reference dye is independent of oxygen levels. The dyes 28a and 28b are thus selected such that the wavelengths of their respective emitted light (spectra) do not overlap and are in the visible light range or in the near infrared light range, in some embodiments. With the emitted light being in the visible range or in the near infrared light range, it can be captured by an optical data detector such as a spectrometer or a digital camera 24a. In some embodiments the spectrometer or digital camera may be incorporated into a smartphone or the like.

In one embodiment of the system 10, the digital camera 24a records an image as a combination of Red (R), Green (G) and Blue (B). In an RGB image, for example, the oxygen sensing dye 28a may emit light in the red portion of the visible spectrum and the reference dye 28b may emit light in the green spectrum. The image can then be digitally split in the RGB components and the pixel intensities of the red and green components can be quantified using digital image software as part of processor 26a. Although in the instant exemplary embodiment, the red and green or red and blue spectra intensities are mainly noted, a third dye, that may be excitable at the same wavelength, but emitting light in either the blue or green spectra, may be added as a part of the cocktail functioning as an additional sensor, detecting another variable or chemical. For example, the green-emitting pH-sensitive fluorescein-based dye can be used in conjunction with the red-emitting oxygen-sensing dye and a blue-emitting reference dye.

In respect to the above description, in the system 10 of the instant disclosure, for example a contact lens 20 having a chemical-sensing dye 28a and a reference dye 28b incorporated therein or applied thereto and digital imaging equipment 24 (FIGS. 3 and 4) is provided. The digital imaging device 24a, in some embodiments, may contain a long-pass light filter in front of the camera lens which is provided to substantially only allow longer (i.e. blue, green, red) wavelengths into the camera, to prevent excitation light from interfering with the image. With reference to FIGS. 3 and 4, the contact lens 20 is installed into the eye of an individual and an operator places the digital imaging device 24a at a predetermined distance from the eye. The excitation light source 24b is then turned on so as to cause excitation of the sensing dye 28a and the reference dye 28b and an RGB image is taken with the digital imaging device 24a. Using digital imaging software installed on the processor 26a, the image is split into, for example, red, green and blue components. The processor 26a is then used to quantify the pixel intensities of the red (sensing dye) and green or blue (reference dye), in the instant exemplary embodiment. Note, that in some embodiments, as discussed above, more than one sensing dye, for example in the green spectrum (if the reference dye is a blue-emitting one), may be used to measure more than one parameter. Using the above-noted equation: $L_{ref}/L_{sens}=K_{sv}[O_2]$ (with respect to oxygen, for example) the amount of oxygen present on the ocular surface of the individual can be ratiometrically determined using the reference dye excited pixel intensity as the baseline so as to provide output 26b, the amount of oxygen present on the ocular surface.

In another embodiment of the system 10, a spectrometer 24a can be used to directly quantify the luminescence from the sensing dye 28a and the reference dye 28b on the contact lens 20. Here, similarly to the above embodiment, the digital imaging software installed on the processor 26a can ratiometrically determine oxygen content on the ocular surface based on for example the red (sensing dye) and green or blue (reference dye) spectral components.

In some embodiments, a dual-emitting (self-referencing) dye may be used. This dye is capable of emitting two distinct luminescence peaks that are respectively dependent and independent of a given chemical or physical-condition, such as oxygen. Here, the fore example oxygen content would be ratiometrically determined from a single dye.

In some embodiments, the excitation light source may be the camera or digital imaging device's 24a flash. In such embodiments, the flash LED light may be modified to emit certain wavelengths of light or a dedicated light filter may be provided in front of the flash so as to filter out unwanted light wavelengths. Alternatively, a dedicated excitation light source 24b, such as an LED excitation light source may be provided.

In some embodiments, a lifetime-detecting complementary metal-oxide-semiconductor (CMOS) image sensor may be used as an alternative detector of luminescence quenching.

EXAMPLES

Example 1—the Peak Emission Spectra of the Oxygen Sensing Contact Lens Dyes Fall within the Red, Green and Blue Digital Camera Spectral Channels Oxygen Sensor For this embodiment, oxygen-sensing dyes were chosen such that emission spectra match the RGB channels of the digital camera chip and incorporated into an oxygen-sensing film. For example, in this embodiment, oxygen was detected using platinum(II)-5,10,15,20-tetrakis-(2,3,4,5,6-pentafluorophenyl) porphyrin (Pt-TPFPP) as the oxygen-sensing dye. This dye emits in the red spectra (max. at 650 nm) and is able to be read by the red (R) camera channel. The oxygen-independent reference dye used in this embodiment was coumarin 153, which emits in the green spectra (max. 528 nm), and is therefore detected by the green (G) camera channel, and in another embodiment 9,10-Diphenylanthracene (DPA) was used, which emits in the blue spectra (max. 446 nm), and is therefore detected by the blue (B) camera channel. In this part of the study, either the blue (B) or the green (G) camera channel remains unused. However, it is contemplated that in other embodiments and applications, as provided below in EXAMPLE 7, all three channels could be utilized.

Pt-TPFPP was first dissolved in ethanol at 2 mg/ml and coumarin 153 or DPA were dissolved in ethanol/water (9:1 v/v) at 2 mg/ml.

In this embodiment, the biocompatible and oxygen-permeable hydrogel D4 (5% w/w in ethanol/water 9:1 v/v) was chosen as the polymer matrix for the dyes. Dyes were mixed with hydrogel D4 either individually in a 1:4 ratio or together in a 1:1:4 ratio.

To minimize leaching of the dyes out of the hydrogel, as well as to prevent physical interactions between the dyes, we have also incorporated Pt-TPFPP and DPA in polystyrene (PS) and polyacrylonitrile (PAN) microparticles, respectively. The microparticles were prepared by a well-established precipitation method. Briefly, the Pt-TPFPP particles precipitated from a solution of Pt-TPFPP (2 mg) and PS (100 mg) in dimethylformamide (12 ml) upon slow addition of distilled water (32 mL). The DPA-PAN particles precipitated from a solution of DPA (6 mg) and PAN (60 mg) in dimethylformamide (6 ml) upon slow addition of distilled water (14 mL) and subsequent addition of brine (4 mL). The particles were separated by centrifugation and washed multiple times with ethanol and water.

The Pt-TPFPP-PS and DPA-PAN particles were mixed with hydrogel D4 either individually or combined in a 2:1 ratio (e.g., 10 mg Pt-TPFPP-PS, 5 mg DPA-PAN in 1 ml hydrogel D4).

Once mixed, the dye-hydrogel mixture was applied using suitable application means to the eye-contacting side of rigid or soft contact lenses and was allowed to dry overnight.

RGB Imaging Setup

With respect to the instant exemplary embodiment, the imaging setup included an excitation light source and a digital camera with a long-pass filter. Excessive ambient light was avoided.

The excitation wavelengths of Pt-TPFPP, coumarin 153 and DPA overlap around 400 nm (violet/indigo light spectra) and thus are all excitable by the same light spectra. The light source was an LED with the peak emission spectra of 401 nm. Images were acquired by Samsung Note 5 phone digital camera with the following parameters: Manual mode; Raw+jpg; ISO 160; white balance: Fluorescent; shutter speed ≥1/1000 s.

The Raw-format images taken by the Samsung camera were converted into 16-bit Tiff's in Adobe Photoshop. The pixel intensities of Tiff RGB channels were measured using ImageJ software.

To separate LED excitation light from the emitted luminescence, a long pass filter (cut off: 435 nm) was placed in front of the camera lens.

Results

Figure 5:
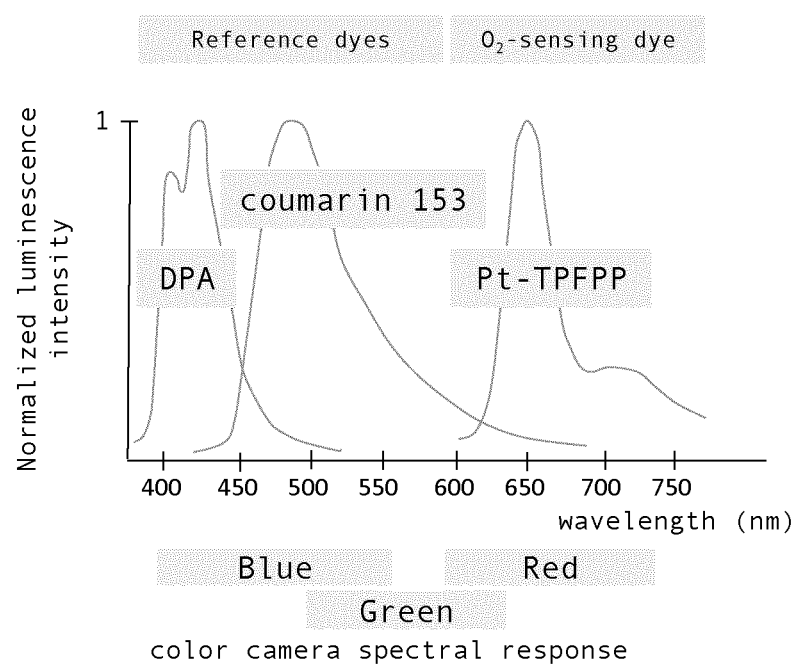
FIG. 5 is a spectral emission graph showing the peaks of Pt-TPFPP, coumarin 153 and DPA in hydrogel excited with indigo light falling within the red, green and blue channels of the visible spectra in an exemplary embodiment.

In the exemplary embodiment with respect to FIG. 5, before combining the oxygen-sensing and reference dyes into a sensor layer, the emission spectra of contact lenses coated with the individual dyes (either neat or embedded in microparticles) in hydrogel were measured. Upon excitation with indigo light at 20% $O_2$, the spectral readings confirmed that the emission peaks of Pt-TPFPP, coumarin 153 and DPA-coated contact lenses indeed fall within the red and green portions of the visible spectra and thus can be detected by red (R), green (G) or blue (B) channels of a digital camera chip, respectively, shown in FIG. 5.

Example 2—the Luminescence Quenching of Oxygen-Sensing Contact Lenses can be Imaged by a Smartphone Camera OXYGEN SENSOR and RGB IMAGING SETUP
As in EXAMPLE 1.

Results

The luminescence quenching of Pt-TPFPP by oxygen had previously been imaged with a digital RGB camera, as noted above. To confirm whether the same approach could be used in the context of oxygen sensing contact lenses, in the exemplary embodiment discussed herein, the luminescence quenching of contact lenses coated with the oxygen-sensing mixture (containing Pt-TPFPP+coumarin 153 or DPA) was quantified.

Figure 6A:
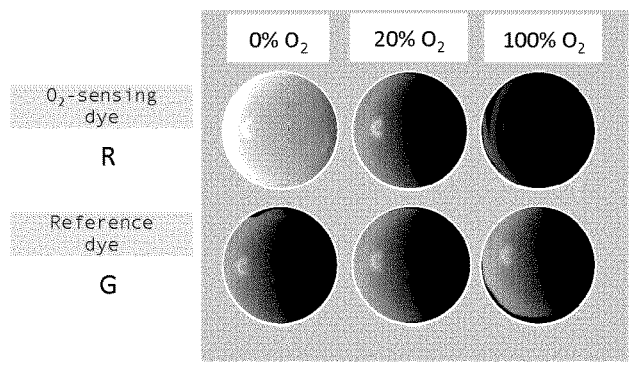
FIG. 6a is a summary of how contact lenses with oxygen-sensing layer of the instant system respond to excitation with three different oxygen levels.

In the exemplary embodiment, the rigid or soft contact lenses were excited with indigo light at 0%, 20% and 100% $O_2$ and the emission was imaged with a smart phone digital camera (RAW image format) (FIG. 6a). The camera exposure values were optimized so as to detect the varying emission intensity without overexposing the signal.

Figure 6B:
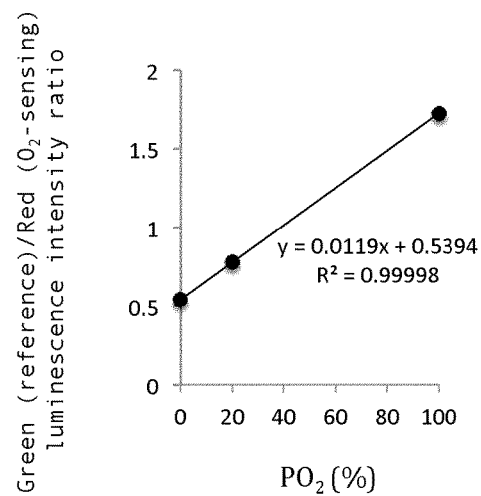
FIG. 6b is a regression plot of oxygen sensor-coated contact lenses of the instant system excited with indigo light at variable $O_2$ levels and imaged by a smart phone camera.

The red (R, $O_2$-sensing emission) and green or blue (G or B, reference emissions) channel pixel intensities of the acquired images were quantified and plotted and the results are shown in FIG. 6b (note that for simplicity only green (G) coumarin reference dye emission is shown here). The ratios of Green (reference emission) and Red ($O_2$-sensing emission) channels follow a linear relationship. Averages of three different measurements are shown for each values.

Example 3—the Luminescence Quenching of Oxygen-Sensing Contact Lenses can be Imaged by a Spectrometer Spectrometry Soft or rigid contact lenses coated with hydrogel-embedded Pt-TPFPP and/or coumarin 153 or DPA were excited with a purple light LED (peak of 401 nm) and UprTEK MK35O spectrometer was used to measure the spectral response (note that for simplicity only green (G) coumarin reference dye emission is shown here). To separate LED excitation light from the emitted luminescence, a long pass filter (cut off: 435 nm) was placed in front of the spectrometer. Excessive ambient light was avoided.

Results

Unlike digital imaging, spectrometry allows for direct analysis of a light signal without the need of converting it first into an RGB image. Therefore to verify the results of the subject pixel intensity method discussed above, a spectrometry test method was used as an alternative way of quantifying the luminescence quenching of the oxygen-sensing dye coated contact lenses. The oxygen-sensing contact lenses were excited with indigo light at 0%, 20% and 100% $O_2$ and the emission was directly read by a spectrometer.

Figure 7A:
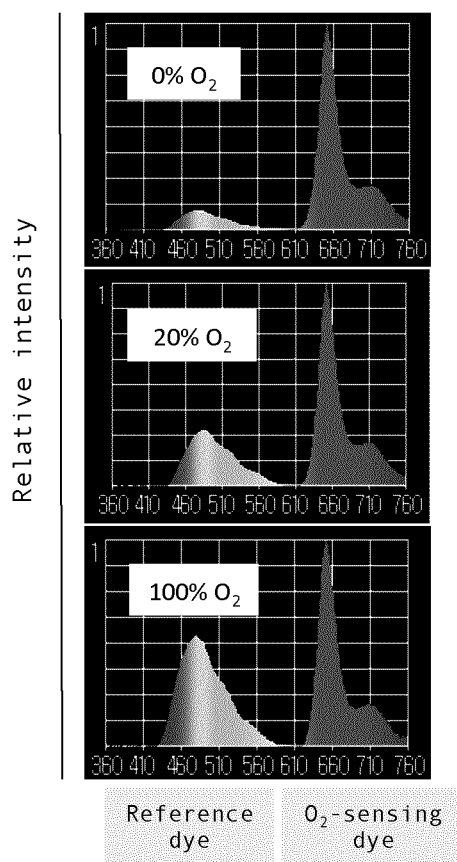
FIG. 7a is a series of three intensity emission spectrum plots for an exemplary embodiment of oxygen-sensing dye-coated contact lenses excited with indigo light at 0%, 20% and 100% $O_2$ levels respectively.
Figure 7B:
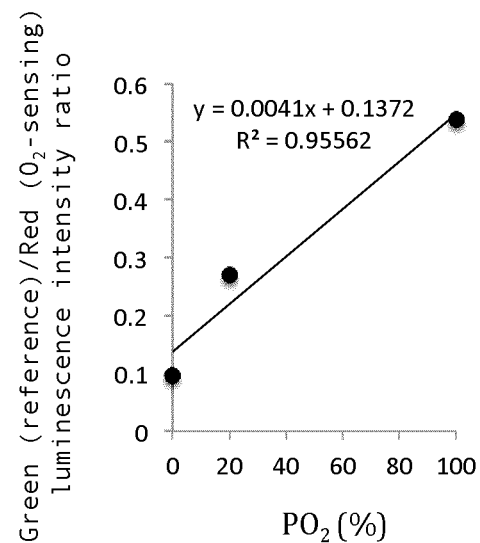

Increasing oxygen levels caused a proportional decrease of the red spectral intensity (Red, $O_2$-sensing emission) as shown sequentially in FIG. 7a (the red emission intensity has the value "1" in every panel). There is shown in these panels a proportional increase in the green spectral component (Green, reference emission) as the level of oxygen increases. Indeed, the ratios of red and green peak values produced a clear linear relationship (FIG. 7b). Thus, spectrophotometry can be used as an alternative and verification method to RGB imaging for quantifying luminescence on the oxygen-sensing contact lens.

FIG. 7b shows the regression of FIG. 7a for 0%, 20% and 100% oxygen concentrations using the averages of three different measurements. Accordingly, using a spectral intensity emission method of quantification, the linear relationship is still followed, indicating that the RGB method discussed above in an exemplary embodiment can be used to accurately quantify oxygen levels in an oxygen-sensing dye coated contact lens.

Example 4—the Luminescence Quenching of Oxygen-Sensing Contact Lenses can be Imaged In Vivo by a Smartphone Camera on the Anterior Ocular Surface of Rabbits Contact Lenses Five sets of contact lenses were used, each set made of polymer with different oxygen permeability: (1) polymethyl methacrylate (PPMA) with zero oxygen permeability and four types of silicone hydrogel of variously high oxygen permeability: (2) somofilcon A (Clarity®1, CooperVision); (3) balafilcon A (PureVision 2, Baush & Lomb); (4) comfilcon A (Biofinity®, CooperVision); and (5) lotrafilocn A (Air Optix® Night & Day®, Alcon). In addition to oxygen permeability, the values of oxygen levels underneath contact lenses of these polymers are also well characterized for rabbit and human corneas. Therefore we have also used these values in our study, namely: 0, 102, 117, 119 and 120 mmHg underneath the six contact lens materials (1-6), respectively. A thin layer of the oxygen sensing mix (2:1 ration of Pt-TPFPP-PS and DPA-PAN in 1 ml hydrogel D4) as described in EXAMPLE 1 was painted on the inner surface of each contact lens.

Animals

Briefly, healthy New Zealand white rabbits (10 weeks of age) were used in this study. All animals were treated strictly in accordance with the ARVO Statement for the Use of Animals in Ophthalmic and Vision Research. Each rabbit was immobilized so that the eyes were unobstructed and easily accessible and anesthetized by the inhalation of isoflurane. The corneal surface of the rabbits was kept moist by the use of a thin layer of artificial tears (Visine® True tears, Johnson & Johnson, Canada). Rabbits were observed for possible signs of eye irritation, prior, during and after the contact lens placement on to the eye.

RGB Imaging Setup

As in EXAMPLE 1.

Results

In the exemplary embodiment, the contact lenses were carefully placed on to the corneal surface of the rabbit and allowed to sit for 10 min in order for the corneal oxygen levels to equilibrate. Each contact lens was briefly excited by the indigo light LED and the emission was imaged with a smart phone digital camera.

Figure 8A:
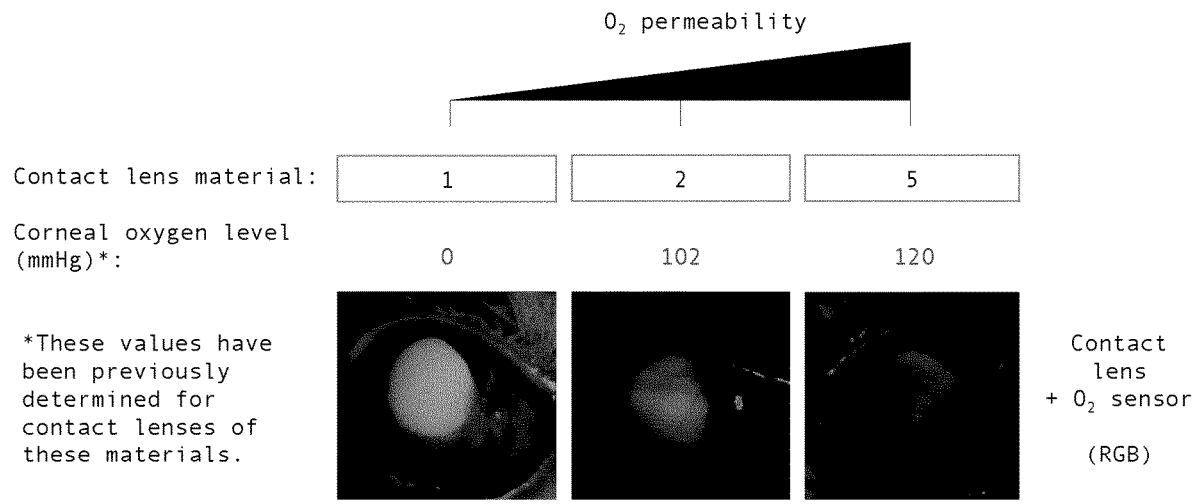
FIG. 8a is an exemplary set of data showing how contact lenses of different oxygen permeabilities with oxygen-sensing layer of the instant system respond to excitation on rabbit corneas with three different oxygen levels.

The oxygen-sensing layer responded very well to the three different corneal oxygen levels and the color difference of the contact lenses of the three different materials were immediately visible (FIG. 8a, top set of exemplary images). Note that both corneal tissue and control contact lenses devoid of the oxygen-sensing layer gave off negligible amount of background luminescence.

Figure 8B:
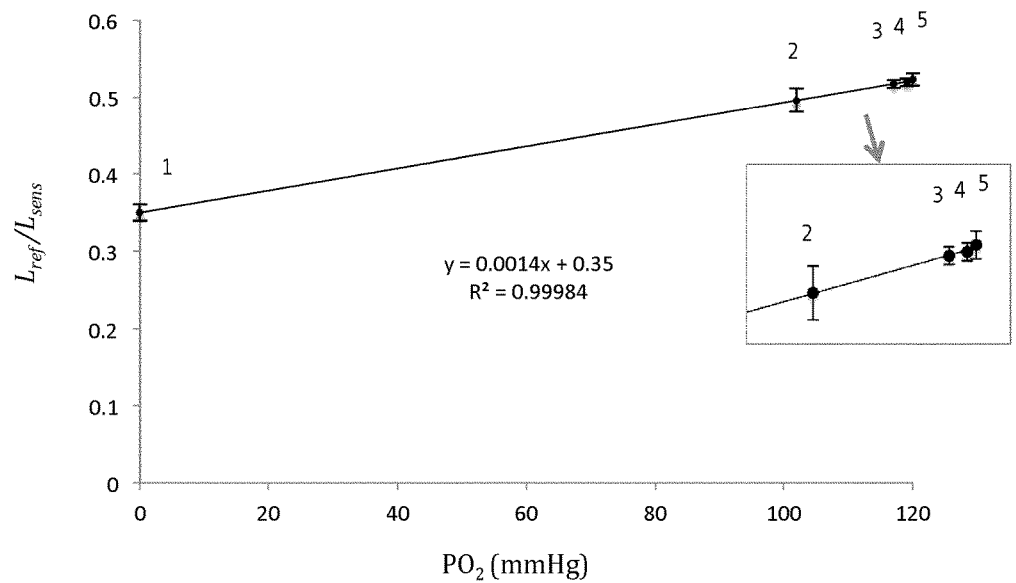
FIG. 8b is a regression plot of oxygen sensor-coated contact lenses of the instant system made of materials with five different oxygen permeabilities, excited with indigo light and imaged with a smart phone camera in an exemplary embodiment.

The red (R, $O_2$-sensing emission) and blue (B, reference emission) channel pixel intensities of the acquired images were quantified and plotted and the results are shown in FIG. 8b. The response of oxygen-sensing dye to varying oxygen levels was excellent. The ratios of Blue (reference emission) and Red ($O_2$-sensing emission) channels produce a clear linear relationship. Averages of three different measurements from three different rabbit eyes using five different contact lenses are plotted.

The response of oxygen-sensing dye to varying oxygen levels was excellent. In this embodiment, it was possible to distinguish among 0.8, 2.5 and 15% differences in tear oxygen levels on the rabbit corneas (120 vs. 119, 117 and 102 mmHg, respectively; FIG. 8b). This indicates that the exemplary embodiment of the instant disclosure is capable to distinguish changes in tear oxygen levels compatible with those observed in diabetic patients. Moreover, the sensitivity of the exemplary system even allows us to detect tear oxygen level changes >10-times smaller than those associated with later stage diabetes (0.8% vs. 10-20%, respectively). This level of sensitivity confirms the validity of our instantly disclosed system and method in detection of early stages of diabetes and pre-diabetes as well as other contexts where minute changes in tear oxygen may serve as biomarkers of underlying disorders.

Example 5: The Oxygen-Sensing Contact Lens is not Cytotoxic to Human Corneal Epithelial Cells Bio Compatibility Assay To demonstrate the oxygen-sensing layer is safe for the use on human corneal tissue, the biocompatibility of the sensing layer and its individual components was assessed in vitro using the well-established cultured human corneal epithelial cell system.

Briefly, silicone hydrogel contact lenses that were either uncoated (serving as controls) or coated with the oxygen-sensing layer were placed on human corneal cells cultured either on a flat or a curved surface for 24 or 72 hrs. The individual components (hydrogel D4, all dyes either neat or embedded in polymeric microparticles) were added directly to the corneal epithelial cell culture media at the following concentrations: 0.25 and 0.5 µg/ml for 24 hrs. At the end of the experimental period, the corneal epithelial cells were harvested and cell viability was assessed using the standard MTT assay (a colorimetric assay for assessing cell metabolic activity, reflecting the number of viable cells present).

Results

Figures 9A, 9B:
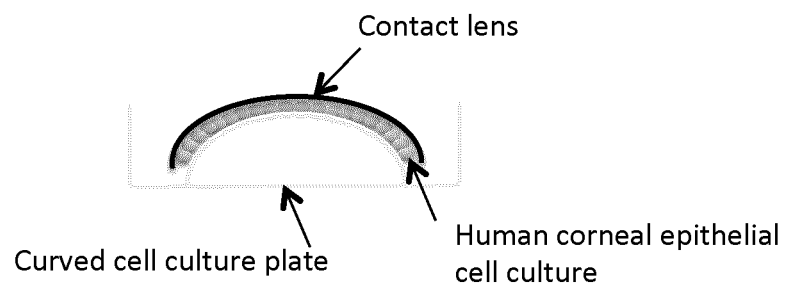
FIG. 9a is a schematics of the experimental design for the biocompatibility testing of the oxygen-sensing contact lenses of the instant system.
FIG. 9b is an exemplary set of data demonstrating the biocompatibility of the oxygen-sensing contact lenses of the instant system.

Neither the sensing and reference dyes (either neat or embedded in polymeric microparticles) nor the oxygen sensing contact lenses had any significant effect on the viability of cultured human corneal epithelial cells and can be therefore considered not cytotoxic to human corneal cells when used in the context of our current prototype. In FIG. 9, an exemplary set of data is shown obtained from an experiment where contact lenses were placed on a curved human corneal cell culture (FIG. 9a) for 72 hrs. The viability of the cultured corneal cells that were exposed to the oxygen-sensing contact lenses (86+7%) was not significantly different from the uncoated contact lens controls (91+12%) (FIG. 9b).

Example 6—the Oxygen-Sensing Contact Lens can be Equipped with Additional Sensing Dyes, Such as a pH-Sensing Dye Dual Oxygen-pH Sensor For the purposes of manifesting the modifiable and expandable character of the contact lens sensing layer, in the exemplary embodiment the hydrogel D4 mix further contained the pH dye, fluorescein isothiocyanate (FITC). FITC was dissolved in ethanol/water (9:1 v/v) at 2 mg/ml and mixed with DPA, Pt-TPFPP and hydrogel D4 in 1:1:1:4 ration, respectively. As before, once mixed, the dye-hydrogel mixture was applied using suitable application means to the eye-contacting side of rigid or soft contact lenses and was allowed to dry overnight.

RGB Imaging Setup

As in EXAMPLE 1.

Results

Figure 10:
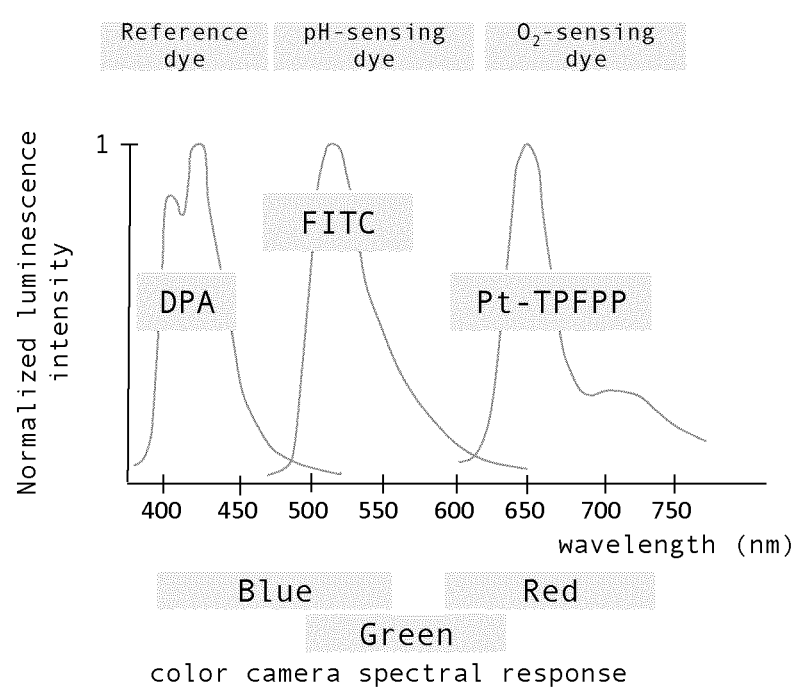
FIG. 10 is a spectral emission graph showing the peaks of Pt-TPFPP, FITC and DPA in hydrogel excited with indigo light falling within the red, green and blue channels of the visible spectra in an exemplary embodiment.

Before combining the oxygen-sensing and reference dyes into a sensor layer, the emission spectra of rigid or soft contact lenses coated with the individual dyes (either neat or embedded in microparticles) in hydrogel were measured. Upon excitation with indigo light at 20% $O_2$, the spectral readings confirmed that the emission peaks of Pt-TPFPP, DPA and FITC-coated contact lenses indeed fall within the red and green portions of the visible spectra and thus can be detected by red (R), green (G) or blue (B) channels of a digital camera chip, respectively, shown in FIG. 10.

Example 7—Smartphone Camera Imaging of the Dual Oxygen-pH Sensing Contact Lens Layer DUAL OXYGEN-pH SENSOR and RGB IMAGING SETUP As in EXAMPLE 6 and 1.

Results

The simultaneous luminescence quenching of Pt-TPFPP and MC by oxygen and pH changes had previously been imaged with a digital RGB camera, as noted above. To confirm whether the same approach could be used in the context of oxygen-pH dual sensing contact lenses, in the exemplary embodiment discussed herein, the luminescence quenching of contact lenses coated with the oxygen-sensing mixture (containing Pt-TPFPP+FITC+DPA) was quantified.

Figure 11A:
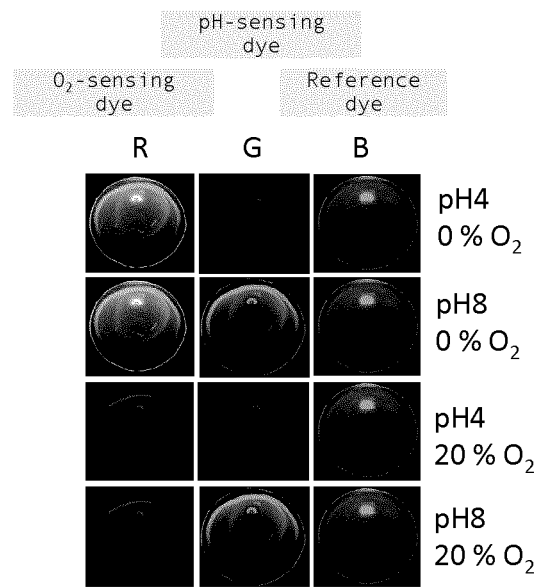
FIG. 11a is a summary of how contact lenses with the dual oxygen-pH-sensing layer of the instant system respond to excitation with different oxygen and pH levels.

In this embodiment, the contact lenses were excited with indigo light at 0%, 20% and 100% $O_2$ and the emission was imaged with a smart phone digital camera (RAW image format) (FIG. 11a). The camera exposure values were optimized so as to detect the varying emission intensity without overexposing the signal.

Figure 11B:
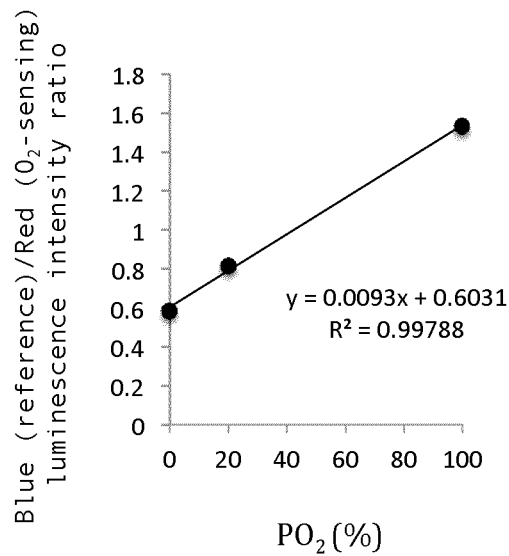
FIG. 11b is a regression plot of dual oxygen-pH sensor-coated contact lenses of the instant system, excited with indigo light and imaged with a smart phone camera in an exemplary embodiment.
Figure 11C:
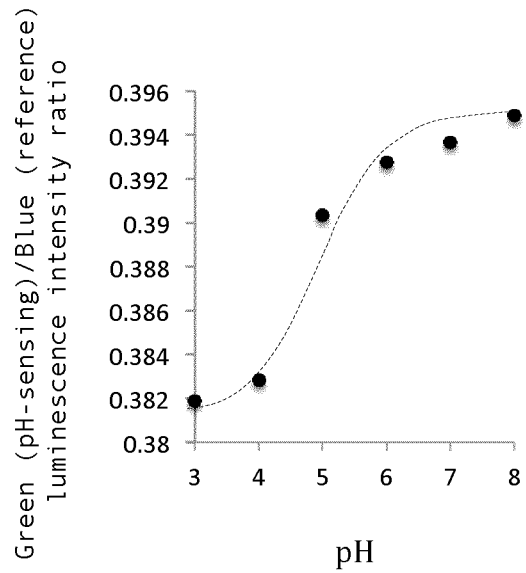
FIG. 11c is a pH calibration curve of dual oxygen-pH sensor-coated contact lenses of the instant system, excited with indigo light and imaged with a smart phone camera in an exemplary embodiment.

The red (R, $O_2$-sensing emission), green (G, pH-sensing emission) or blue (B, reference emission) channel pixel intensities of the acquired images were quantified and plotted and the results are shown in FIGS. 11b and 11c. The ratios of Blue (reference emission) and Red ($O_2$-sensing emission) channels follow a linear relationship (FIG. 11b). The ratios of Blue (reference emission) and Green (pH-sensing emission) channels produce the typical sigmoidal pH calibration curve (FIG. 11c). Averages of three different measurements are shown for each plots.

We claim:

1. A system for detecting or assessing a condition in ocular tissues, the system comprising:
    a composition for contacting at least one ocular tissue, the composition comprising a photo-reactive indicator dye and a photo-reactive reference dye, each dye being responsive to substantially the same wavelength of light from an excitation light source, each dye luminescing at different wavelengths of the light spectrum, the photo-reactive indicator dye being responsive to the condition and the photo-reactive reference dye being non-responsive to the condition;
    an optical detector for receiving light emitted from each dye to generate an optical data set;
    a processor for processing the optical data set to determine the luminescence intensity of the different wavelengths emitted by each dye, and ratiometrically comparing the luminescence intensity from the photo-reactive indicator dye wavelengths relative to the luminescence intensity from the photo-reactive reference dye wavelengths.

2. The system of claim 1, wherein the photo-reactive indicator dye is any one of a porphyrin-based dye, a metalloporphyrin dye, or a polycyclic aromatic hydrocarbon-based dye.

3. The system of claim 2, wherein the photo-reactive indicator dye is responsive to oxygen or carbon dioxide.

4. The system of claim 2, wherein the photo-reactive indicator dye is responsive to at least one of $Na^+$, $K^+$ or $H^+$.

5. The system of claim 2, wherein the photo-reactive indicator dye is responsive to temperature.

6. The system of claim 2, wherein the composition is a membrane with an outer layer of variable permeability.

7. The system of claim 1, wherein the composition is a membrane with an outer layer of variable permeability.

8. The system of claim 1, wherein the composition is a liquid when applied to the at least one ocular tissue.

9. The system of claims 1, wherein the condition is indicative of microcirculatory dysfunction, prediabetes, or diabetes.

10. The system of claim 1, wherein the condition is indicative of an ocular disorder.

11. The system of claim 1, wherein the condition is indicative of any one of glaucoma, neurogenic optic atrophy, pseudoexfoliation syndrome, ischaemic ocular syndrome, uveitis, retinal vein occlusion, retinopathy, hypertensive retinopathy, diabetic retinopathy, or diabetic macular edema.

12. The system of claim 1, wherein the composition comprises a second photo-reactive indicator dye responsive to a second condition.

13. The system of claims 1, wherein the luminescence intensities are ratiometrically compared based on pixel intensity.

14. A method for detecting a condition in ocular tissues using a smart phone camera, the method comprising:
    receiving an emitted light from a photo-reactive indicator dye and a photo-reactive reference dye, and
    generating a digital image for assessing a relative luminescence intensity of different wavelengths of the emitted light, the photo-reactive indicator dye being responsive to the condition and the photo-reactive reference dye being non-responsive to the condition.

15. The method of claim 14, wherein the condition is indicative of microcirculatory dysfunction, prediabetes, or diabetes.

16. A contact lens for use in the detection of a condition in ocular tissues, the contact lens having a photo-reactive indicator dye and a photo-reactive reference dye applied thereto to emit light in response to an excitation light source to permit ratiometric comparison based on relative luminescence intensity of different wavelengths of the emitted light, the photo-reactive indicator dye being responsive to the condition and the photo-reactive reference dye being non-responsive to the condition.

* * * * *